United States Patent
Onishi

(10) Patent No.: US 9,826,961 B2
(45) Date of Patent: Nov. 28, 2017

(54) ULTRASONIC TRANSDUCER ELEMENT PACKAGE, ULTRASONIC TRANSDUCER ELEMENT CHIP, PROBE, PROBE HEAD, ELECTRONIC DEVICE, ULTRASONIC DIAGNOSTIC APPARATUS, AND METHOD FOR PRODUCING ULTRASONIC TRANSDUCER ELEMENT PACKAGE

(71) Applicant: SEIKO EPSON CORPORATION, Tokyo (JP)

(72) Inventor: Yasunori Onishi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 1192 days.

(21) Appl. No.: 13/917,070

(22) Filed: Jun. 13, 2013

(65) Prior Publication Data
US 2013/0338502 A1    Dec. 19, 2013

(30) Foreign Application Priority Data

Jun. 14, 2012 (JP) .................................. 2012-134560

(51) Int. Cl.
| | |
|---|---|
| A61B 8/00 | (2006.01) |
| A61B 8/13 | (2006.01) |
| H01L 41/25 | (2013.01) |
| B06B 1/06 | (2006.01) |

(52) U.S. Cl.
CPC .............. *A61B 8/4494* (2013.01); *A61B 8/13* (2013.01); *A61B 8/4483* (2013.01); *B06B 1/0629* (2013.01); *H01L 41/25* (2013.01); *A61B 8/00* (2013.01); *Y10T 29/42* (2015.01)

(58) Field of Classification Search
CPC ........ A61B 8/4494; A61B 8/13; A61B 8/4483
See application file for complete search history.

(56) References Cited

U.S. PATENT DOCUMENTS 6,974,417 B2 * 12/2005 Lockwood ............ B06B 1/0622
                                                                                                        600/459
2002/0045829 A1    4/2002   Nakamura et al.
2007/0013264 A1    1/2007   Wilser et al.
(Continued)

FOREIGN PATENT DOCUMENTS

| JP | 63-128899 A | 6/1988 |
|---|---|---|
| JP | 2009-200771 A | 9/2009 |

(Continued)

OTHER PUBLICATIONS

The extended European Search Report for European Application No. 13172012.0 dated Dec. 17, 2013.

*Primary Examiner* — Joseph M Santos Rodriguez
(74) *Attorney, Agent, or Firm* — Global IP Counselors, LLP

(57) ABSTRACT

An ultrasonic transducer element package includes a first substrate, a second substrate, a support body, and first and second ultrasonic transducers. The first substrate has first and second openings that are aligned in a first direction. The second substrate has a third and fourth openings that are aligned in the first direction. The support body supports the first and second substrates. The first and second substrates are aligned in a second direction that intersects with the first direction, with a space therebetween. The first and Second ultrasonic transducer elements are configured at the first and second openings respectively.

14 Claims, 11 Drawing Sheets

(56) References Cited

U.S. PATENT DOCUMENTS

2009/0207560 A1* 8/2009 Lee .................... H01L 51/5243
361/679.01
2011/0252890 A1 10/2011 Matsuda
2011/0263982 A1 10/2011 Kano

FOREIGN PATENT DOCUMENTS

| JP | 2010-279426 A | 12/2010 |
| JP | 2011-082624 A | 4/2011 |
| JP | 2013-144063 A | 7/2013 |

* cited by examiner

ULTRASONIC TRANSDUCER ELEMENT PACKAGE, ULTRASONIC TRANSDUCER ELEMENT CHIP, PROBE, PROBE HEAD, ELECTRONIC DEVICE, ULTRASONIC DIAGNOSTIC APPARATUS, AND METHOD FOR PRODUCING ULTRASONIC TRANSDUCER ELEMENT PACKAGE

CROSS-REFERENCE TO RELATED APPLICATIONS

This application claims priority to Japanese Patent Application No. 2012-134560 filed on Jun. 14, 2012. The entire disclosure of Japanese Patent Application No. 2012-134560 is hereby incorporated herein by reference.

BACKGROUND

Technical Field

The present invention relates to an ultrasonic transducer element package, an ultrasonic transducer element chip, a probe, a probe head, an electronic device, an ultrasonic diagnostic apparatus, and a method for producing ultrasonic transducer element package.

Related Art

As is disclosed in, for example, Patent Document 1, an ultrasonic transducer element chip is provided with a single substrate. A pair of openings is formed on the substrate. An ultrasonic transducer element is provided to each of the openings. The ultrasonic transducer elements are provided with a vibrating film. The vibrating film closes off the opening from the surface of the substrate. Ultrasonic waves are generated in response to vibration of the vibration film at each of the ultrasonic transducer elements.

Japanese Laid-open Patent Publication No. 2011-82624 (Patent Document 1) and Japanese Laid-open Patent Publication No. 63-128899 (Patent Document 2) are examples of the related art.

SUMMARY

In a thin-film ultrasonic transducer element, generating vibration involves forming a piezoelectric body at each of the vibrating films disposed on the substrate. The ultrasonic transducer elements need not be cut out into individual pieces from the substrate, as per the bulk-type piezoelectric body element disclosed in Patent Document 2. On the other hand, in order to narrow the focal point of the scan direction of an ultrasonic beam, there has been a desire to broaden the interval between ultrasonic transducer elements in the scan direction. The beam width of the focal point of the ultrasonic beam can be adjusted in accordance with such intervals. Broadening the intervals between transducer elements in the ultrasonic wave scan direction in this manner in this manner can result in the creation of a useless substrate region that does not contribute to transmitting or receiving ultrasonic waves between the openings of the substrate.

According to one aspect of the invention, an ultrasonic transducer element package includes a first substrate, a second substrate, a support body, and first and second ultrasonic transducers. The first substrate has first and second openings that are aligned in a first direction. The second substrate has a third and fourth openings that are aligned in the first direction. The support body supports the first and second substrates. The first and second substrates are aligned in a second direction that intersects with the first direction, with a space therebetween. The first and Second ultrasonic transducer elements are configured at the first and second openings respectively.

According to another aspect of the invention, a method for producing an ultrasonic transducer element package includes preparing a first substrate having first and second openings that are aligned in a first direction, preparing a second substrate having third and fourth openings that are aligned in the first direction, preparing a support body supporting the first and second substrates, where the first and second substrates are aligned in a second direction that intersects with the first direction; and configuring first and second ultrasonic transducer elements at the first and second openings respectively.

According to another aspect of the invention, an ultrasonic transducer element package includes a first substrate, a first substrate vibrating film, a first piezoelectric element, a second substrate, a second substrate vibrating film, a second piezoelectric element, and a support body. The first substrate has first and second openings that are aligned in a first direction. The first substrate vibrating film are arranged to close off the first and second openings. The first piezoelectric element is configured at the first and second opening on the first substrate vibrating film. The second substrate has third and fourth openings that are aligned in a second direction. the second substrate vibrating film is arranged to close off the third and fourth openings. The second piezoelectric element is configured at the third and fourth openings, on the second substrate vibrating film. The support body supports the first and second substrates. The first and second substrates are aligned in a second direction, with a space therebetween. The first direction are parallel to the second direction.

BRIEF DESCRIPTION OF THE DRAWINGS

Referring now to the attached drawings which form a part of this original disclosure.

DETAILED DESCRIPTION OF EXEMPLARY EMBODIMENTS

The following describes embodiments of the invention, with reference to the accompanying drawings. The present embodiments described below are not, however, meant to gratuitously limit the content of the invention described in the claims, nor is the entire configuration described in the present embodiments necessarily essential in terms of the solution of the invention.

(1) Overall Configuration of the Ultrasonic Diagnostic Apparatus

Figure 1:
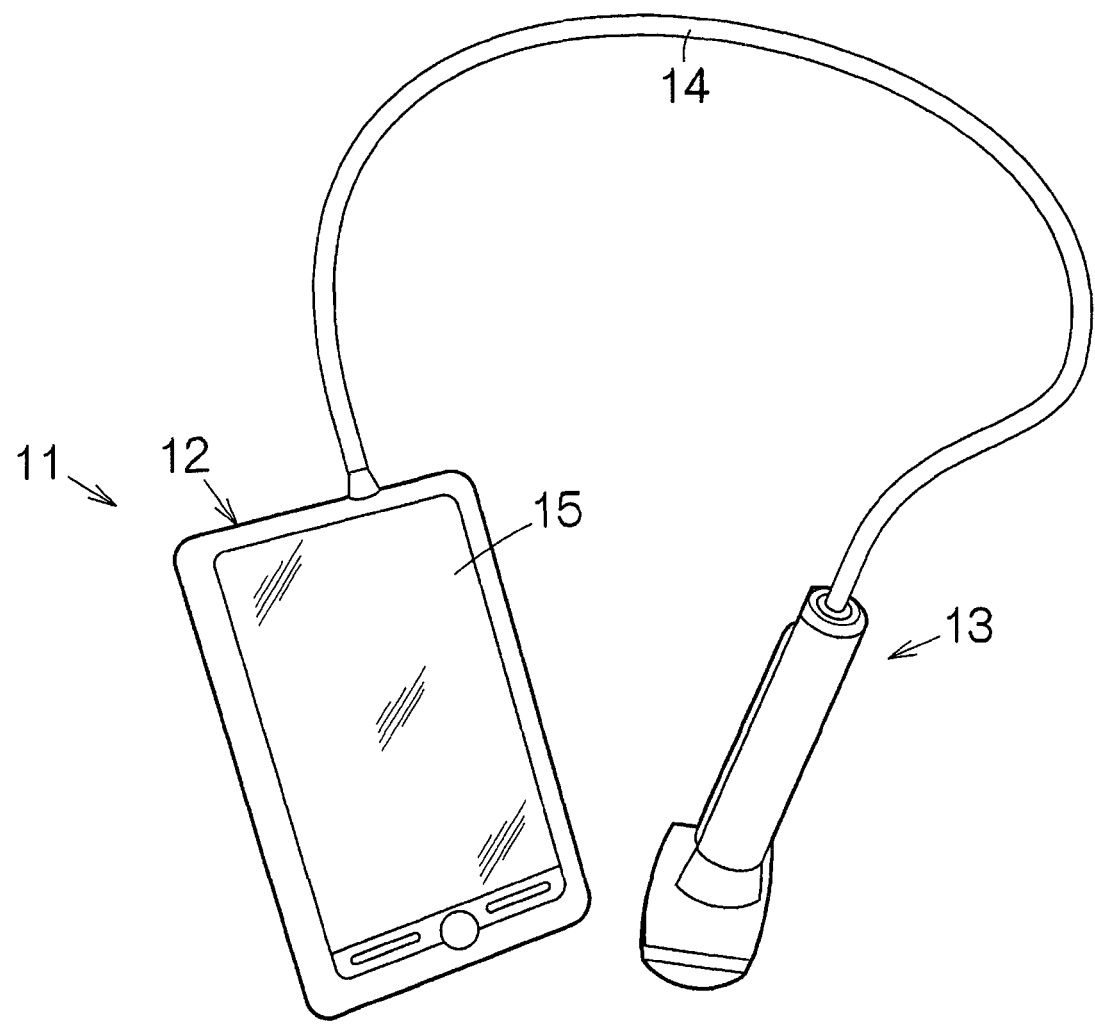
FIG. 1 is an external view schematically illustrating one embodiment of an electronic device as in an embodiment, i.e., an ultrasonic diagnostic apparatus.

FIG. 1 schematically illustrates one embodiment of an electronic device as in an embodiment of the invention, i.e., an ultrasonic diagnostic apparatus 11. The ultrasonic diagnostic apparatus 11 is provided with an apparatus terminal 12 and an ultrasonic probe (probe) 13. The apparatus terminal 12 and the ultrasonic probe 13 are connected to each other with a cable 14. The apparatus terminal 12 and the ultrasonic probe 13 exchange electrical signals with each other through the cable 14. A display panel (display device) 15 is incorporated into the apparatus terminal 12. A screen of the display panel 15 is exposed on the surface of the apparatus terminal 12. In the apparatus terminal 12, as will be described below, an image is generated on the basis of ultrasonic waves detected by the ultrasonic probe 13. A visualized detection result is displayed on the screen of the display panel 15.

Figure 2:
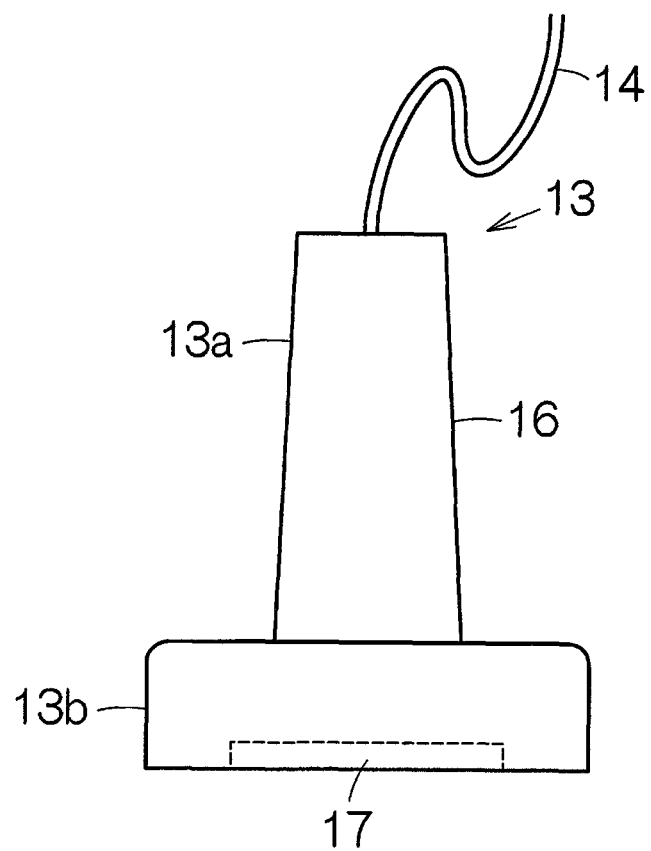
FIG. 2 is an enlarged front view of an ultrasonic probe.

As is illustrated in the FIG. 2, the ultrasonic probe 13 has a housing 16. The housing 16 accommodates an ultrasonic transducer element package (hereinafter "element package") 17. A surface of the element package 17 can be exposed at the surface of the housing 16. The element package 17 both outputs ultrasonic waves from the surface and receives reflected waves of the ultrasonic waves. Additionally, the ultrasonic probe 13 can be provided with a probe head 13b that is detachably connected to a probe body 13a. Herein, the element package 17 can be incorporated into the housing 16 of the probe head 13b.

Figure 3:
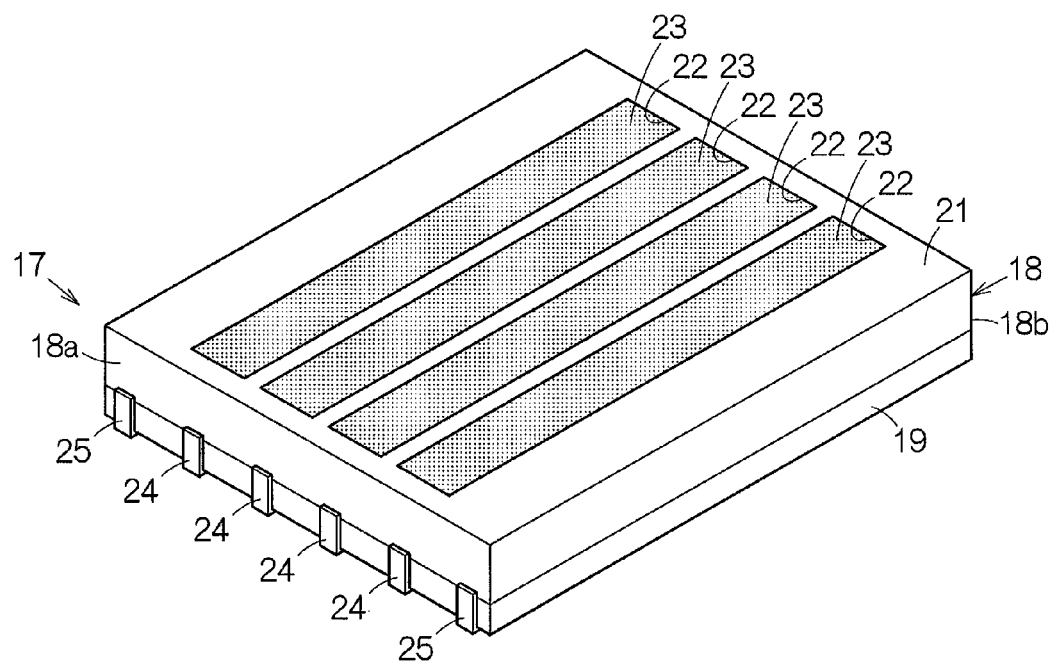
FIG. 3 is an enlarged perspective view of an ultrasonic transducer element package.

FIG. 3 schematically illustrates the exterior appearance of the element package 17 as in the first embodiment. The element package 17 is provided with a support body 18. The support body 18 is provided with a plate member (planar part) 19. An enclosure wall 21 is coupled to a surface of the plate member 19. The enclosure wall 21 arises from a plate surface of the plate member 19 and encloses a plurality of recesses 22 along the plate surface of the plate member 19. The plate member 19 and the enclosure wall 21 are coupled to each other in an air-tight fashion.

Each of the recesses 22 is formed in an elongated rectangular parallelepiped. Each of the recesses 22 is arranged side by side in parallel. The rectangular parallelepipeds extend in parallel to each other from a first side surface 18a of the support body 18 toward a second side surface 18b on the opposite side. Each of the recesses 22 is filled with a resin material 23. For the resin material 23, it would be possible to use, for example, a silicone resin.

At the first side surface 18a of the support body 18, a first electroconductive terminal 24 is arranged for each of the recesses 22. The first electroconductive terminals 24 are fixed to the first side surface 18a. A pair of second electroconductive terminals 25 is arranged on the two sides of the arraying of the first electroconductive terminals 24. That is, the arraying of the first electroconductive terminals 24 is arranged between the one pair of second electroconductive terminals 25. The second electroconductive terminals 25 are fixed to the first side surface 18a of the support body 18. Each of the first electroconductive terminals 24 and the second electroconductive terminals 25 can wrap around an end surface of the plate member 19 from the surface of the plate member 19 and reach as far as a back surface of the plate member 19. The first electroconductive terminals 24 and the second electroconductive terminals 25 are also arranged in a similar fashion at the second side surface 18b on the opposite side of the first side surface 18a (not shown here). The first electroconductive terminals 24 and the second electroconductive terminals 25 can be formed of, for example, a metal material such as copper, or another electroconductive material.

Figure 4:
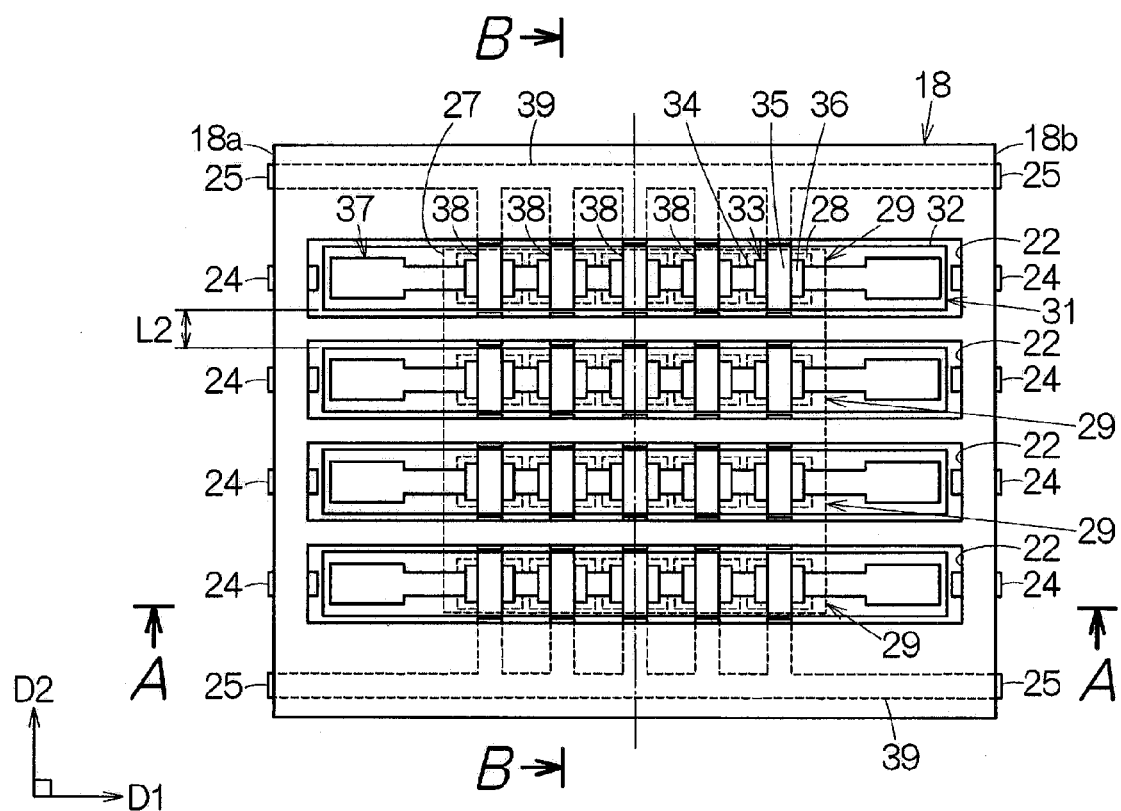
FIG. 4 is a perspective plan view of an ultrasonic transducer element package.

As is illustrated in FIG. 4, an element array 27 is formed on the support body 18. The element array 27 is constituted of an array of ultrasonic transducer elements (hereinafter "elements) 28. The array is formed of a matrix of a plurality of rows and a plurality of columns. In the forming of the matrix, a plurality of ultrasonic transducer element columns (hereinafter "element columns") 29 are arranged side by side in parallel. An element column 29 is constituted of the ultrasonic transducer elements 28 arranged side by side in a column (a single column) in a first direction D1.

An ultrasonic transducer element chip (hereinafter "element chip") 31 is incorporated into each of the recesses 22. The element chip 31 is provided with an elongated substrate 32. In this manner, a plurality of elongated substrates 32 are arranged side by side with an interval spacing in a second direction D2 that intersects with the first direction D1 on the surface of the plate member 19. Herein, the second direction D2 is orthogonal to the first direction D1. All of the substrates 32 are formed in the same shape. Herein, the substrates 32 are formed of silicon. As shall be described below, the substrates 32 can be cut out from a single substrate, i.e. from a silicon wafer. A distance L2 between the substrates 32 in the second direction D2 is defined by the distance between the ends of neighboring substrates 32.

A single element column 29 is formed in each of the substrates 32. Each of the elements 28 is provided with a piezoelectric element part 33. The piezoelectric element section 33 is constituted of a lower electrode (first electrode) 34, an upper electrode (second electrode) 35, and a piezoelectric body film 36. In each of the elements 28, the piezoelectric body film 36 is interposed between the lower electrode 34 and the upper electrode 35.

One first electroconductor 37 is formed on each of the substrates 32. The first electroconductors 37 extend in the longitudinal direction of the substrates 32 from one end of the substrates 32 to the other end. The first electroconductor 37 is formed to be shared by one column of elements 28. The first electroconductor 37 forms the lower electrode 34 for each of the elements 28.

Second electroconductors 38 of the same number as the elements 28 are formed on each of the substrates 32. The second electroconductors 38 are insulated from the first electroconductors 37. Each of the second electroconductors 38 extends in a direction that crosses over the longitudinal direction of the substrates 32. Herein, the second electroconductors 38 extend in a direction orthogonal to the longitudinal direction of the substrates 32. The second electroconductors 38 are formed in each of the elements 28. Each of the second electroconductors 38 is insulated from each other. The second electroconductors 38 form the upper electrode 35 in each of the elements 28.

A third electroconductor 39 is formed on two sides of the arraying of the element columns 29 in the support body 18. The third electroconductors 39 extend, for example, in parallel to the element columns 29 on the outside of the element array 27. The third electroconductors 39 are connected to each of the second electroconductive terminals 25 on both ends. In this manner, the third electroconductors 39 extend between the second electroconductive terminals 25 of the first side surface 18a and the second electroconductive terminals 25 of the second side surface 18b. As shall be described below, all of the second electroconductors 38 are connected to the third electroconductors 39.

Power distribution to the elements 28 is switched for each of the substrates 32. A line scan or a sector scan is implemented in accordance with such switching of power distribution. One column of the elements 28 outputs ultrasonic waves at the same time, and thus the number in one column, i.e., the number of rows in the arraying can be determined in accordance with the output level of the ultrasonic waves. The number of rows can be set to, for example, about ten to 15. Though omitted in the drawings, there are five rows drawn. The number of columns in the arraying can be determined in accordance with the spread of the range of the scan. The number of columns can be set to, for example, 128 columns or 256 columns. Though omitted in the drawings, there are four columns drawn. Otherwise, a staggered arrangement can also be established in the array. With a staggered arrangement, an element group of an even-numbered column can be shifted by one-half of a row pitch with respect to an element group of an odd-numbered column. The number of elements of one among either the odd-numbered columns or the even-numbered columns can be one less than the number of elements in the other. Furthermore, the first electroconductors 37 can form the upper electrode of the piezoelectric element section 33, whereas the second electroconductors 38 can form the lower electrode of the piezoelectric element section 33.

Figure 5:
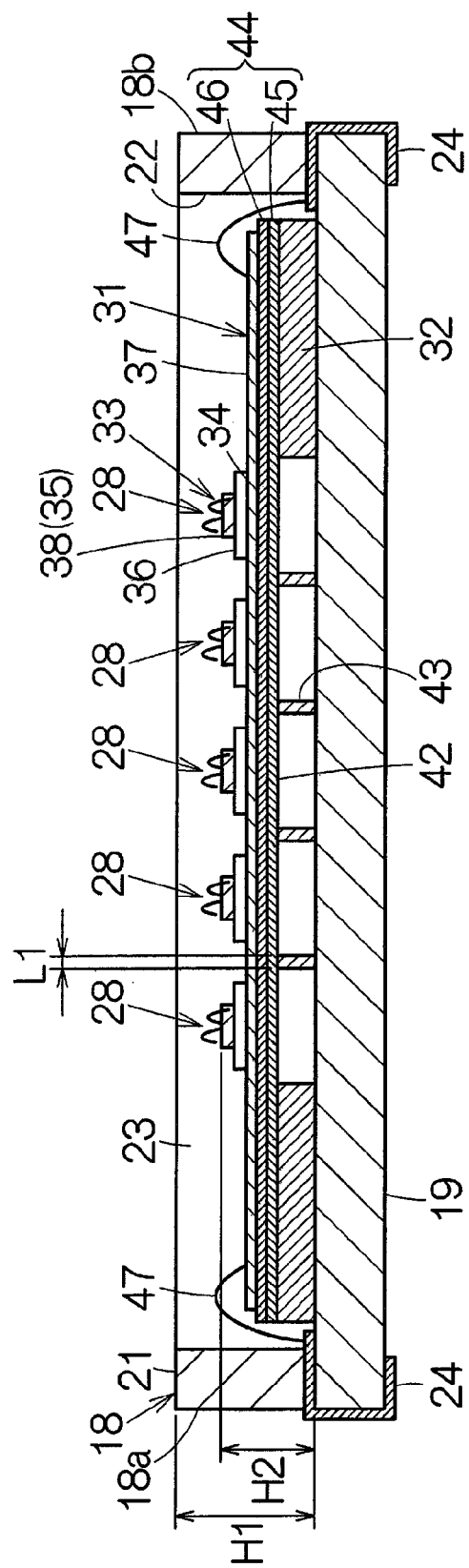
FIG. 5 is a vertical cross-sectional view taken along the A-A line in FIG. 4.

As is illustrated in FIG. 5, each of the elements 28 has a vibrating film 42. In the forming of the vibrating films 42, an opening 43 is formed in each of the elements 28 on the substrates 32. The openings 43 are arranged side by side in one column in the longitudinal direction of the substrates 32. The distance L1 between the openings 43 in the first direction D1 is defined by the distance between outer edges of neighboring openings 43. The distance L1 between the openings 43 is smaller than the distance L2 between the substrates 32. A flexible film 44 is formed over the full surface of the substrates 32. The flexible film 44 is constituted of a silicon oxide (SiO2) layer 45 stacked onto the surface of the substrate 32 and a zirconium oxide (ZrO2) layer 46 stacked onto the surface of the silicon oxide layer 45. The flexible film 44 is in contact with the openings 43. In this manner, parts of the flexible film 44 function as the vibrating films 42 so as to correspond with the outline of the openings 43. The film thickness of the silicon oxide layer 43 can be determined on the basis of the resonance frequency. The resonance frequency is equivalent to the frequency of the ultrasonic waves.

The first electroconductors 37, the piezoelectric body films 36, and the second electroconductors 38 are layered in the stated order onto the surface of the vibrating films 42. The first electroconductors 37 cross over the openings 43 of one column of openings 43. For the first electroconductors 37, it would be possible to use, for example, a multilayer film of titanium (Ti), iridium (Ir), platinum (Pt), and titanium (Ti). The piezoelectric body films 36 can be formed of, for example, lead zirconate titanate (PZT). The second electroconductors 38 can be formed of, for example, iridium (Ir). The second electroconductors 38 cross over the openings 43 separately at each of the openings 43. Different electroconductive materials can be used for the first electroconductors 37 and the second electroconductors 38, and different piezoelectric materials can be used for the piezoelectric body film 36. Herein, the piezoelectric body films 36 completely cover the lower electrodes 34 below the upper electrodes 35. A short circuit can be avoided between the upper electrodes 35 and the lower electrodes 34 by the action of the piezoelectric body films 36.

Each of the first electroconductive terminals 24 projects out into the recesses 22. The first electroconductors 37 are connected at one end to the first electroconductive terminals 24 of the first side surface 18a and are connected at the other end to the first electroconductive terminals 24 of the second side surface 18b. In each of the connections, it would be possible to use, for example, one electroconductive wire 47. This electroconductive wire 47 can be formed by, for example, wire bonding. In this manner, the wiring of one first electroconductor 37 can be drawn out to the outside of the support member 18.

As will be understood from FIG. 5, the substrates 32 and the elements 28 are accommodated within the recesses 22, which are enclosed by the enclosure wall 21. The enclosure wall 21 forms the recesses that enclose the substrates 32. A height H1 of the enclosure wall 21 is greater than a height H2 of the elements 28, and thus the resin material 23 covers over the elements 28. The surfaces of the substrates 32 are covered with the resin material 23. The resin material 23 is able to function as an acoustic matching layer on the surface of the vibrating films 42. The acoustic matching layer is responsible for adjusting the acoustic impedance between the vibrating films 42 and a subject, and for preventing the ultrasonic waves from being reflected.

Figure 6:
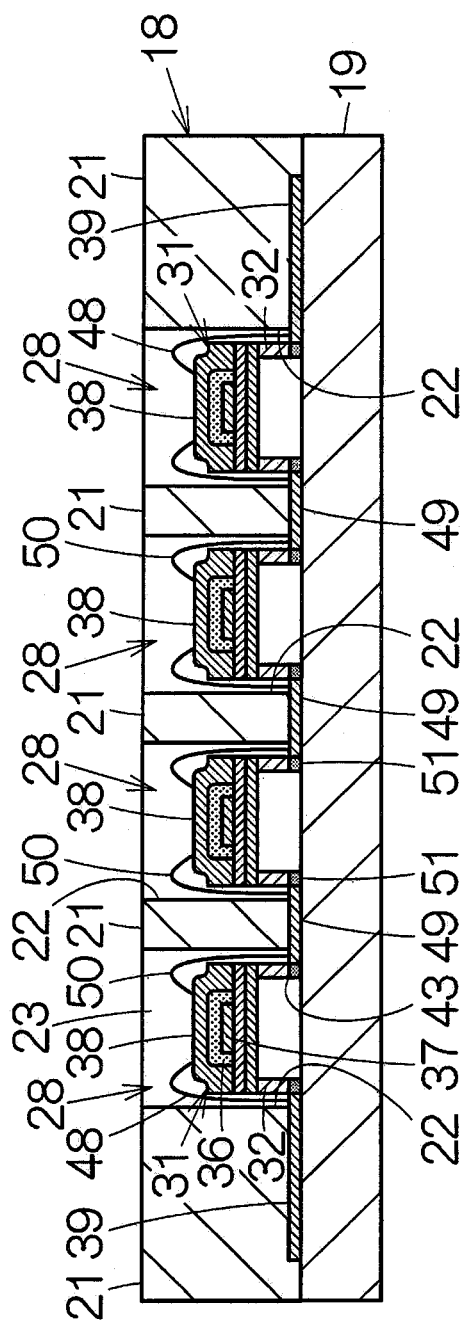
FIG. 6 is a vertical cross-sectional view taken along the B-B line in FIG. 4.

As is illustrated in FIG. 6, the second electroconductors 38 are connected to the third electroconductors 39. In the connections, the third electroconductors 39 project out at each of the elements 28 in the recesses 22 closest to the third electroconductors 39. The second electroconductors 38 are connected to the third electroconductors 39 by, for example, a single electroconductive wire 48. This electroconductive wire 48 can be formed by, for example, wire bonding. In addition, between the element columns 29, fourth electroconductors 49 are arranged in between the enclosure wall 21 and the plate member 19. The fourth electroconductors 49 are arranged with reference to one row of the elements 28. The fourth electroconductors 49 project out into the recesses 22 on the two sides of the enclosure wall 21. The second electroconductors 38 are connected to the fourth electroconductors 49 by, for example, a single electroconductive wire 50. This electroconductive wire 50 can be formed by, for example, wire bonding. In this manner, the second electroconductors 38 are electrically connected through the fourth electroconductors 49 at neighboring recesses 22. As a result, the second electroconductors 38 corresponding to one row of the elements 28 are connected to each of the third electroconductors 39 on both ends of the one row. In this manner, the wiring of all the second electroconductors 38 can be drawn out to the outside of support body 18 in common through the third electroconductors 39.

As will be understood from FIG. 6, the element chip 31 is anchored to the plate member 19 of the support body 18, with an adhesive layer 51. The adhesive layer 51 is sandwiched between the plate member 19 and the substrates 32. Herein, the adhesive layer 51 is an adhesive agent that is cured and manifests an adhesive function, and is less rigid than the substrates 32 and the plate member 19 of the support body 18.

(2) Circuit Configuration of the Ultrasonic Diagnostic Apparatus

Figure 7:
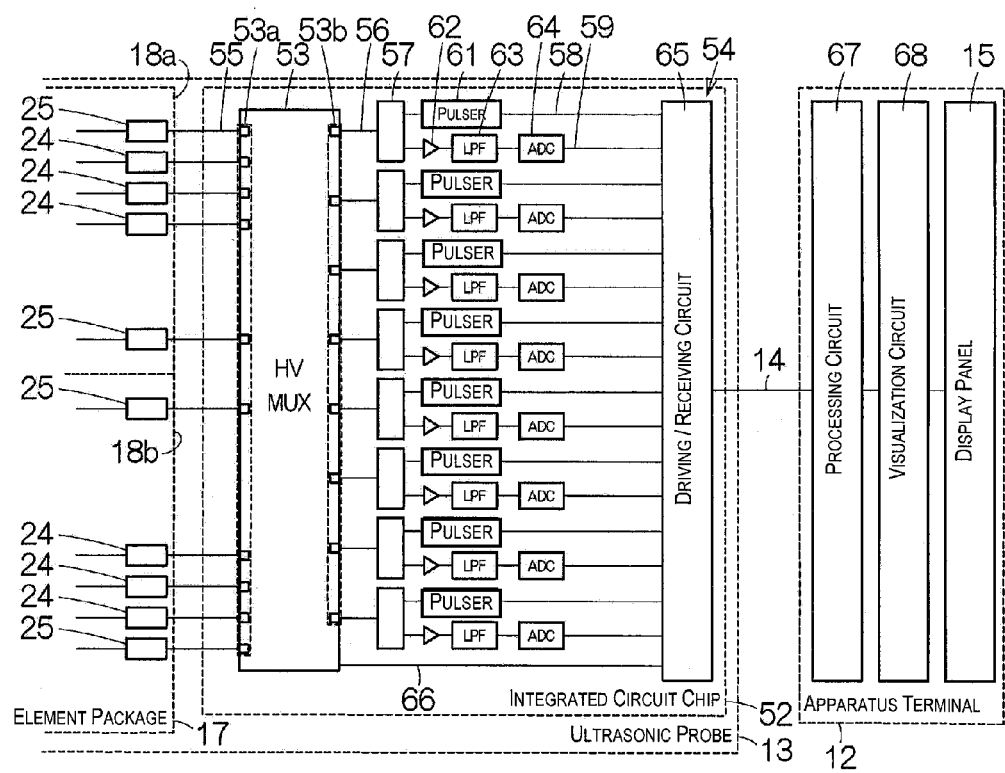
FIG. 7 is a block diagram schematically illustrating a circuit configuration of an ultrasonic diagnostic apparatus.

As is illustrated in FIG. 7, the ultrasonic diagnostic apparatus 11 is provided with an integrated circuit chip 52 that is electrically connected to the element package 17. The integrated circuit chip 52 is provided with a multiplexer 53 and a transceiver circuit 54. The multiplexer 53 is provided with a port group 53a on the side of the element package 17 and with a port group 53b on the side of the transceiver circuit 54. The first electroconductive terminals 24 and the second electroconductive terminals 25 are connected to the port group 53a on the side of the element package 17 via signal lines 55. In this manner, the port group 53a leads to the element array 27. Herein, a defined number of signal lines 56 within the integrated circuit chip 52 are connected to the port group 53b on the side of the transceiver circuit 54. The defined number is equivalent to the number of columns of elements 28 that produce an output at the same time during a scan. The multiplexer 53 manages the mutual connections between ports on the side of the cable 14 and ports on the side of the element package 17.

The transceiver circuit 54 is provided with a defined number of selector switches 57. Each of the selector switches 57 is connected to the respectively corresponding individual signal line 56. The transceiver circuit 54 is provided with a transmission path 58 and a reception path 59 for each of the selector switches 57. The transmission path 58 and the reception path 59 are connected in parallel to the selector switches 57. The selector switches 57 selectively connect either the transmission path 58 or the reception path 59 to the multiplexer 53. A pulser 61 is incorporated into the transmission path 58. The pulser 61 outputs a pulse signal at a frequency corresponding to the resonance frequency of the vibrating films 42. An amplifier 62, a low-pass filter (LPF) 63, and an analog-to-digital converter (ADC) 64 are incorporated into the reception path 59. A detection signal of each of the element 28 is amplified and converted into a digital signal.

The transceiver circuit 54 is provided with a driving/receiving circuit 65. The transmission path 58 and the reception path 59 are connected to the driving/receiving circuit 65. The driving/receiving circuit 65 controls the pulsers 61 at the same time in accordance with the format of the scan. The driving/receiving circuit 65 receives the digital signal of the detection signal in accordance with the format of the scan. The driving/receiving circuit 65 is connected to the multiplexer 53 by a control line 66. The multiplexer 53 implements management of the mutual connections on the basis of a control signal supplied from the driving/receiving circuit 65.

A processing circuit 67 is incorporated into the apparatus terminal 12. The processing circuit 67 can be provided with, for example, a central processing unit (CPU) and a memory. The overall operation of the ultrasonic diagnostic apparatus 11 is controlled in accordance with the processing of the processing circuit 67. The processing circuit 67 controls the driving/receiving circuit 65 in accordance with an instruction inputted from a user. The processing circuit 67 generates an image in accordance with the detection signals of the elements 28. The image is specified with visualization data.

A visualization circuit 68 is incorporated into the apparatus terminal 12. The visualization circuit 68 is connected to the processing circuit 67. The display panel 15 is connected to the visualization circuit 68. The visualization circuit 68 generates a drive signal in accordance with visualization data generated by the processing circuit 67. The drive signal is fed to the display panel 15. As a result, an image is displayed on the display panel 15.

(3) Operation of the Ultrasonic Diagnostic Apparatus

The following is a simple description of the operation of the ultrasonic diagnostic apparatus 11. The processing circuit 67 sends to the driving/receiving circuit 65 an instruction to transmit and receive ultrasonic waves. The driving/receiving circuit 65 both supplies a control signal to the multiplexer 53 and supplies a drive signal to each of the pulsers 61. The pulsers 61 output a pulse signal in response to the supplying of the drive signal. The multiplexer 53 connects ports of the port group 53a to ports of the port group 53b in accordance with the instruction of the control signal. The pulse signals are supplied to the elements 28 in each of the columns through the first through fourth electroconductors 37, 38, 39, 49 in accordance with the selection of the ports. The vibrating films 42 vibrate in response to the supplying of the pulse signals. As a result, desired ultrasonic waves are emitted toward the subject (for example, the interior of a human body).

After the transmission of the ultrasonic waves, the selector switches 57 are switched. The multiplexer 53 maintains the connecting relationships between the ports. The selector switches 57 establish connections between the receiving paths 59 and the signal lines 56, instead of connections between the transmission paths 58 and the signal lines 56. Reflected waves from the ultrasonic waves cause the vibrating films 42 to vibrate. As a result, detection signals are outputted from the elements 28. The detection signals are converted into digital signals and fed to the driving/receiving circuit 65.

The ultrasonic waves are repeatedly transmitted and received. During the repetition, the multiplexer 53 alters the connecting relationships between the ports. As a result, a line scan or sector scan is implemented. When the scan is complete, the processing circuit 67 forms an image on the basis of the digital signal of the detection signal. The image thus formed is displayed on the screen of the display panel 15.

In the element package 17, the element chips 31 are incorporated into the recesses 22. Recesses 22 that are adjacent to each other are separated from one another by the enclosure wall 21. As such, the substrates 32 of the element chips 31 are arranged spaced apart from each other on the support body 18. As a result, the substrate material between the substrates 32 can be forgone. Any desired interval between neighboring element columns 29 can be set, while also achieving a reduction in the substrate material. In this manner, when any desired interval between the element columns 29 can be set, the degree of freedom in the focal length of the ultrasonic beam can be broadened.

As described above, the substrate 32 is formed of a highly rigid material, such as Si or glass. In each of the substrates 32, the intervals between the openings 43 can be held securely. A constant ultrasonic beam can be formed at each of the substrates 32. This manner of holding the ultrasonic beam can contribute to simplifying the design of the element package 17.

In each of the element chips 31, the one first electroconductor 37 crosses over the one column of the openings 43. The first electroconductor 37 forms the lower electrode 34, in common with the one column of the piezoelectric body films 36. The drawing out of the wiring from the lower electrodes 34 can thus be simplified.

In the element package 17, the recesses 22 are spaced apart from each other by the enclosure wall 21. In addition, each of the recesses 22 is filled with the resin material 23. As such, the space between neighboring substrates 32 is filled in with an insulator material. The insulator material acts to make it possible to readily hold the intervals between the substrates 32.

As described above, the support body 18 is provided with the plate member 19 and the enclosure wall 21. The recesses 22 are enclosed by the enclosure wall 21, and the lower ends of the recesses 22 are closed off by the plate member 19. In the formation of the acoustic matching layer, the resin material (the acoustic matching layer material) 23 in a fluid form can be poured into the inside of the enclosure wall 21 from the openings of the recesses 22. The acoustic matching layer can be formed easily. This manner of simplifying production can contribute to reducing the product costs.

The solid adhesive layer 51 is sandwiched between the support body 18 and the substrates 32. The adhesive layer 51 can be of lower rigidity than that of the support body 18 and the substrates 32. When the less rigid adhesive layer is interposed between the hard support body 18 and substrates 32 in this manner, the adhesive layer can absorb the vibration of the substrates 32. When the vibrating films 42 vibrate, the transmission of vibration toward the support body 18 can be reduced. As such, cross-talk is reduced. The signal-to-noise (S/N) ratio is enhanced.

(4) Method for Producing an Ultrasonic Transducer Element Chip

Figure 8:
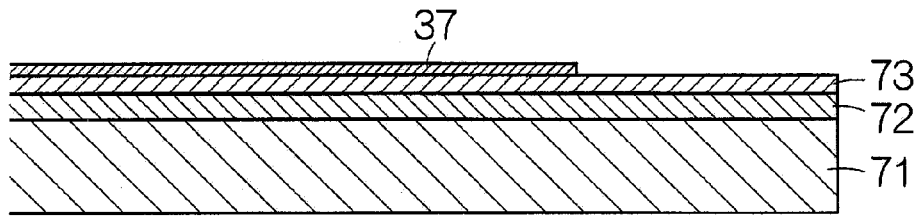
FIG. 8 is a partially enlarged vertical cross-sectional view schematically illustrating a first electroconductor and a flexible film formed on a silicon wafer.

As illustrated in FIG. 8, a group of the first electroconductors 37 is formed on the surface of a silicon wafer (substrate) 71. The first electroconductors 37, which are of the same shape, can be arranged side by side in parallel. Prior to the formation of the first electroconductors 37, a silicon oxide film 72 and a zirconium oxide film 73 are formed in the stated order on the surface of the silicon wafer 71. A film of an electroconductive material is formed on the surface of the zirconium oxide film 73. The film of the electroconductive material is constituted of a laminated film of iridium, platinum, and titanium. The first electroconductors 37 are formed from an electroconductive film on the basis of a photolithography technique.

Figure 9:
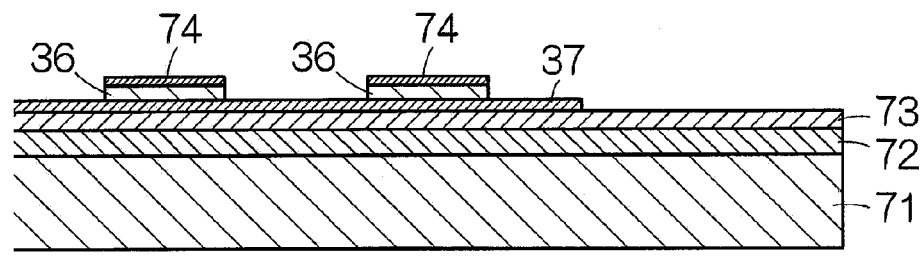
FIG. 9 is a partially enlarged vertical cross-sectional view schematically illustrating a first electroconductive film and a piezoelectric body film formed on a first electroconductor.

As illustrated in FIG. 9, the piezoelectric body film 36 and a first electroconductive film 74 are formed for each of the elements 28 on the surface of the first electroconductor 37. In the formation of the piezoelectric films 36 and the first electroconductive films 74, a film of a piezoelectric material and a film of an electroconductive material are deposited on the surface of the silicon wafer 71. The film of the piezoelectric material is constituted of a PZT film. The film of the electroconductive material is constituted of an iridium film. The piezoelectric body films 36 and the first electroconductive films 74 are formed from the film of the piezoelectric material and the film of the electroconductive material for each of the elements 28 on the basis of a photolithography technique.

Figure 10:
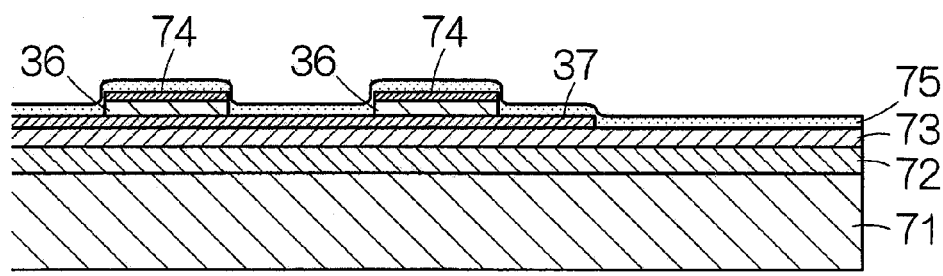
FIG. 10 is a partially enlarged vertical cross-sectional view schematically illustrating a film of an electroconductive material for covering a silicon wafer.

Next, as illustrated in FIG. 10, a film 75 of an electroconductive material is deposited on the surface of the silicon wafer 71. The film 75 of the electroconductive material covers the first electroconductive film 74. Then, a second electroconductive film is formed from the film 75 of the electroconductive material on the basis of a photolithography technique. The second electroconductive film extends in a direction orthogonal to the first electroconductors 37, and crosses over the first electroconductors 37 one by one in succession. The second electroconductive film connects the first electroconductive films 74 in the row direction. The first electroconductive films 74 and the second electroconductive films constitute the second electroconductors 38. Herein, the first electroconductive films 74 are equivalent to a lower layer of the upper electrodes 35.

Figure 11:
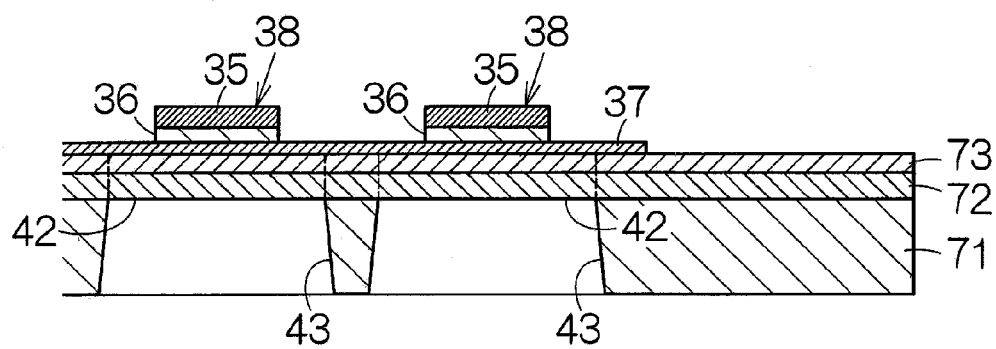
FIG. 11 is a partially enlarged vertical cross-sectional view schematically illustrating openings formed in a silicon wafer.

Thereafter, as illustrated in FIG. 11, the array of the openings 43 is formed from the back surface of the silicon wafer 71. The formation of the openings 43 involves performing an etching treatment. The silicon oxide film 72 functions as an etching stop layer. The vibrating films 42 are demarcated into the silicon oxide film 72 and the zirconium oxide film 73.

Figure 12:
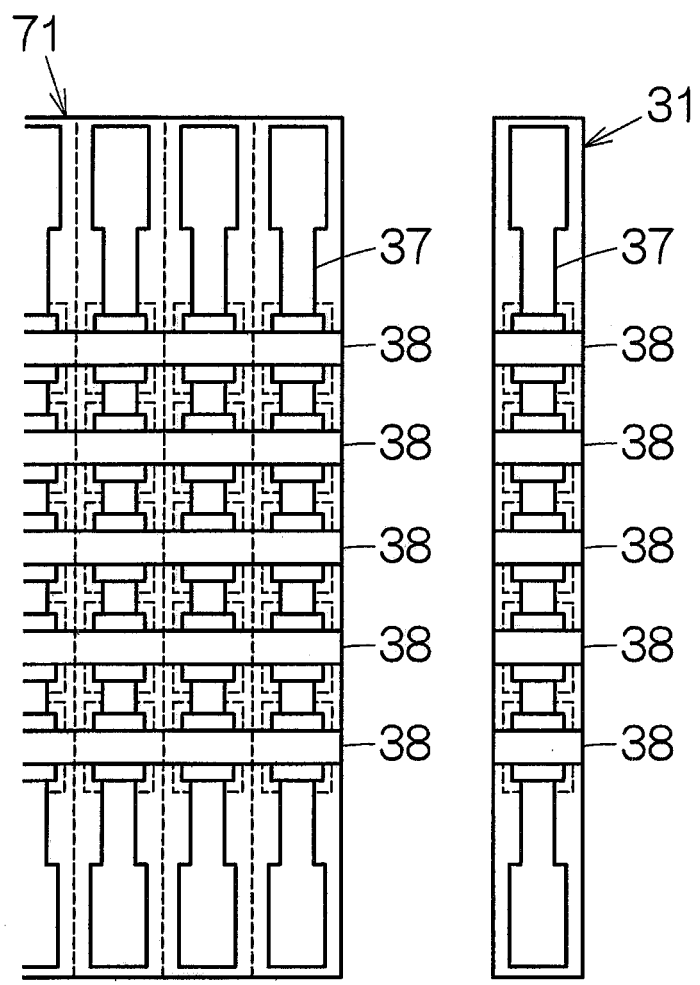
FIG. 12 is an enlarged plan view schematically illustrating an ultrasonic transducer element chip that is cut out from a silicon wafer.

After the formation of the openings 43, as illustrated in FIG. 12, the silicon wafer is cut at each of the element columns 29 connected by the first electroconductors 37. In this manner, the element chip 31 is produced. The cut-out element chips 31 are arranged side by side in parallel with each other, spaced apart by intervals, on the support body 18. As described above, each of the element chips 31 is accommodated in the recesses 22 of the support body 18. The arrangement of the element chips 31 involves preemptively preparing the support body 18. The support body 18 is formed by bonding the enclosure wall 21 to the plate member 19. The plate member 19 and the enclosure wall 21 can be molded from, for example, a hard resin material. Prior to the bonding, the first electroconductive terminals 24, the second electroconductive terminals 25, and the third and fourth electroconductors 39, 49 are formed on the plate member 19. The element chips 31 are fixed to the surface of the plate member 19 by the adhesive layer 51. Thereafter, the electroconductive wires 47, 48 are formed. After the formation of the electroconductive wires 47, 48, the resin material 23 (acoustic matching layer material) in a fluid form is poured into the recesses 22.

The first electroconductors 37, the piezoelectric body films 36, the second electroconductors 3, and the openings 43, which are equivalent to one element chip 31, can be formed in repeating pattern on one silicon wafer 71. The element chips 31 can be easily formed in the same shape. When the element chips 31 are standardized in this manner, the element package 17 can be addressed to a variety of usages by changing the design of the support body 18. The delivery time can be curtailed and costs can be reduced.

(5) Ultrasonic Transducer Element Package as in the Second Embodiment

Figure 13:
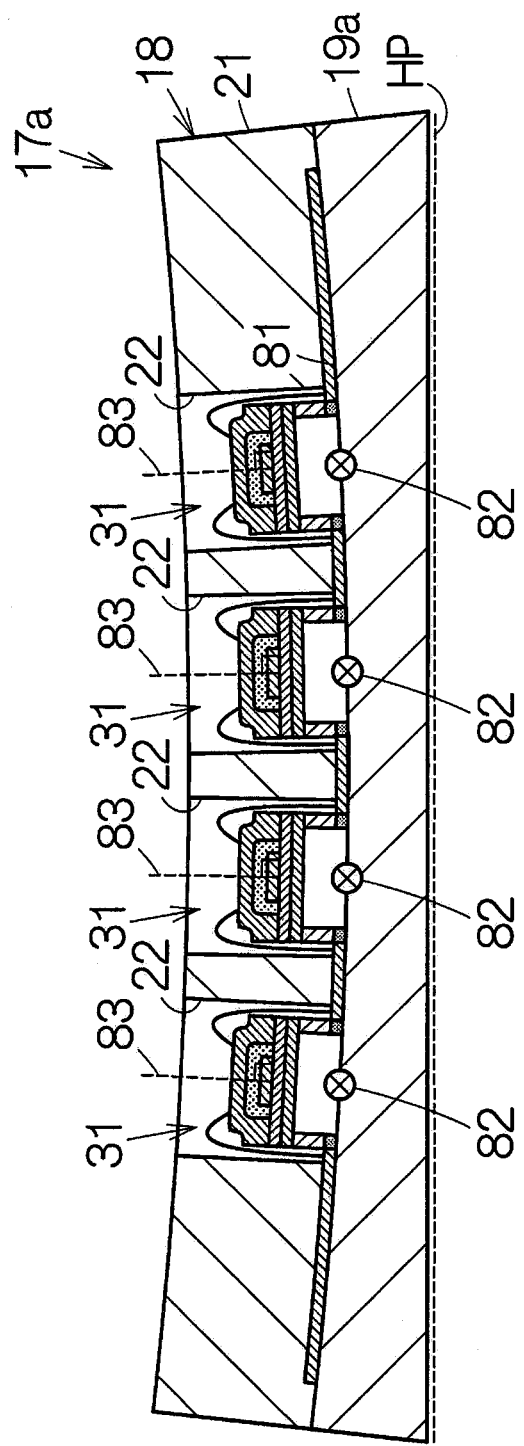
FIG. 13 is a side view schematically illustrating a structure of an ultrasonic transducer element package as in a second embodiment.
Figure 14:
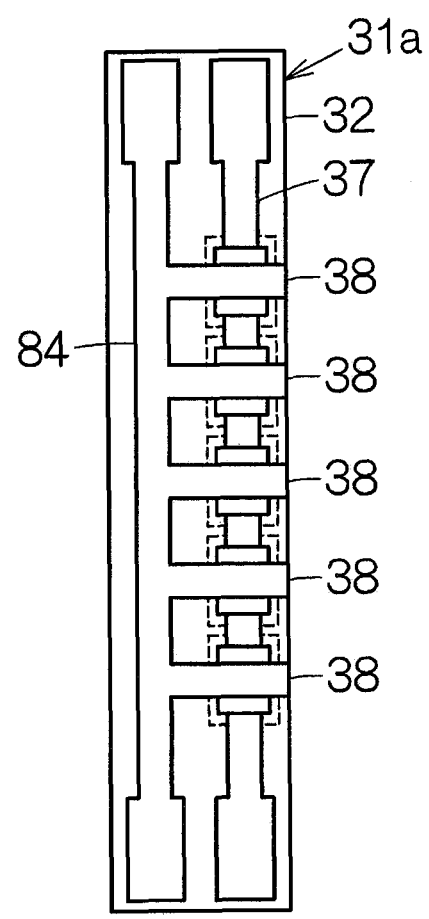
FIG. 14 is an enlarged plan view schematically illustrating an ultrasonic transducer element chip that is incorporated into an ultrasonic transducer element package as in a third embodiment.

FIG. 13 schematically illustrates the structure of an element package 17a as in the second embodiment. With this element package 17a, there is a recessed curved surface 81. The curved surface 81 is defined, for example, by the surface of a plate member 19a. The curved surface 81 has generating lines 82 in parallel with each other. As such, the curvature of the curved surface 81 is specified within a virtual plane orthogonal to the generating lines 82. The curved surface 81 should have a uniform curvature.

The recesses 22 are demarcated following the curved surface 81. Within the recesses 22, the element chips 31 are fixed to the curved surface 81. The element chips 31 are arranged in parallel with the generating lines 82 of the curved surface 81. The vibrating films 42 of each of the elements 28 extends in parallel with a virtual plane that includes the tangent line of the curved surface 81 and the generating lines 8. Herein, the generating lines 82 are specified at regular intervals.

In the element package 17*a* as in the second embodiment, the substrates 32 are arranged so as to match the generating lines 82, which are in parallel with each other. In one row of the elements 28 of the matrix, a vertical line 83 of the vibrating films (42) focuses to a point. As such, the beam width of the ultrasonic beam can be narrowed without an acoustic lens. A thinner or smaller scale can be achieved. Product costs can be reduced.

Herein, a bottom surface of the element package 17*a*, i.e., a back surface of the plate member 19*a* is formed on a plane HP. According to the plane HP of such description, the element package 17*a* can be installed easily on a plane. The first electroconductive terminals 24 and the second electroconductive terminals 25 are arranged along the plane HP, and thus it is easy to establish an electroconductive connection to the first electroconductive terminals 24 and the second electroconductive terminals 25. The plate member 19*a* can be formed at a uniform plate thickness. As such, the bottom surface of the element package 17*a* can be curved. When the plate thickness is set so as to be uniform in this manner, the plate member 19*a* can be easily produced by bending. In addition, a flexible resin can be used for the plate member 19*a* and the enclosure wall 21. The plate member 19*a* and the enclosure wall 21 can be deformed following the shape of the installation surface. As a result, curved surfaces 81 of a variety of curvatures can be provided, depending on the curvature of the installation surface. The element package 17*a* can be addressed to ultrasonic beams of a variety of focal lengths.

(6) Ultrasonic Transducer Element Package as in the Third Embodiment

FIG. 13 illustrates element chips 31*a* used in an element package as in the third embodiment. With the element chips 31*a*, there is one third electroconductor 84 formed in parallel to one first electroconductor 37 on a plate surface of the substrates 32. A third electroconductor 84 is insulated from the first electroconductors 37. The third electroconductor 84 extends in the longitudinal direction of the substrates 32, from one end of the substrates 32 to the other end. The second electroconductors 38 are connected to each of the third electroconductors 84. In this manner, the third electroconductors 84 can be drawn out to the outside of the support body 18 for each of the element chips 31*a*.

Though embodiments have been described in greater detail above, it shall be readily understood by a person skilled in the art that there are numerous possible modifications which do not substantially depart from the novel matter and effects of the invention. As such, the modification examples of such description are all also included in the scope of the invention. For example, in the specification or drawings, a phrase that is mentioned at least once together with a different phrase of the same or broader meaning can be substituted with that different phrase at any point in the specification or drawings as well. Also, the configurations and operations of the ultrasonic diagnostic apparatus 11, the ultrasonic probe 13, the ultrasonic transducer element package 17, 17*a*, the element array 27, the ultrasonic transducer element 28, the control circuit chip 52, and the like are not limited to being what was described in the embodiments, but rather a variety of modifications are possible.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer element package, comprising:
   a first substrate having a first opening and a second opening that are aligned in a first direction;
   a second substrate having a third opening and a fourth opening that are aligned in the first direction;
   a support body having a first surface and a second surface that face away from each other in an opposite direction, the opposite direction intersecting with the first direction, the support body supporting the first substrate and the second substrate at a side of the first surface, the first substrate and the second substrate being aligned in a second direction that intersects with the first direction and the opposite direction, and being spaced apart from each other in the second direction; and
   a first ultrasonic transducer element and a second ultrasonic transducer element being disposed corresponding to the first opening and the second opening, respectively.

2. The ultrasonic transducer element package according to claim 1, wherein
   a distance between the first opening and the second opening in the first direction is smaller than a distance between the first substrate and the second substrate in the second direction.

3. The ultrasonic transducer element package according to claim 1, further comprising
   a first electroconductor that crosses over the first opening and forms a first electrode of the first ultrasonic transducer element; and a second electroconductor that crosses over the first opening and forms a second electrode of the first ultrasonic transducer element.

4. The ultrasonic transducer element package according to claim 1, wherein
the spacing between the first substrate and the second substrate is filled with an insulator material.

5. The ultrasonic transducer element package according to claim 1, wherein
the support body includes a planar part partially forming the first surface on which the first substrate and the second substrate are disposed, and an enclosure wall that arises from the first surface of the planar part and forms, along the surface of the planar part, recesses that enclose the first substrate and the second substrate and the first ultrasonic transducer element and the second ultrasonic transducer element,
the recesses are filled with an acoustic matching layer, and
the acoustic matching layer covers the first ultrasonic transducer element and the second ultrasonic transducer element.

6. The ultrasonic transducer element package according to claim 1, further comprising
an adhesive layer that is interposed between the support body and the first substrate, and between the support body and the second substrate, wherein
the adhesive layer adheres the first substrate and the second substrate to the support body, and is less rigid than the support body and the first substrate and the second substrate.

7. The ultrasonic transducer element package according to claim 1, wherein
the support body has a concave curved surface having generating lines that are in parallel with each other, and
the first substrate and the second substrate are arranged so as to match the generating lines.

8. A probe comprising:
the ultrasonic transducer element package according to claim 1; and
a housing supporting the ultrasonic transducer element package.

9. An electronic device comprising:
the probe according to claim 8; and
a processing circuit being configured to control the first ultrasonic transducer element and the second ultrasonic transducer element to output, the processing circuit being connected to the probe.

10. An ultrasonic diagnostic apparatus comprising:
the probe according to claim 8; and
a processing circuit being configured to control the first ultrasonic transducer element and the second ultrasonic transducer element to output and generate an image, the processing circuit being connected to the probe; and
a display device being configured to display the image.

11. A probe head comprising:
the ultrasonic transducer element package according to claim 1; and
a housing supporting the ultrasonic transducer element package.

12. An ultrasonic transducer element chip, comprising:
a substrate having a plurality of openings that are aligned in a first direction;
a plurality of ultrasonic transducer elements aligned in the first direction and disposed corresponding to the plurality of openings, respectively;
a first electroconductor that continuously crosses over the plurality of the openings and forms a plurality of first electrodes of the plurality of the ultrasonic transducer elements; and
a second electroconductor that forms a plurality of second electrodes of the plurality of the ultrasonic transducer elements, the number of the plurality of the second electrodes being equal to the number of the plurality of the ultrasonic transducer elements, the plurality of the second electrodes crossing over the plurality of the openings, respectively, and being, spaced apart from each other.

13. A method for producing an ultrasonic transducer element package, comprising:
preparing a first substrate which has a first opening and a second opening aligned in a first direction and on which a first ultrasonic transducer element and a second ultrasonic transducer element are formed so as to be disposed corresponding to the first opening and the second opening, respectively;
preparing a second substrate having a third opening and a fourth opening that are aligned in the first direction;
preparing a support body having a first surface and a second surface that face away from each other in an opposite direction, the opposite direction intersecting with the first direction; and
disposing the first substrate and the second substrate at a side of the first surface of the support body such that the first substrate and the second substrate are aligned in a second direction that intersects with the first direction and the opposite direction and are spaced apart from each other in the second direction.

14. An ultrasonic transducer element package, comprising
a first substrate having a first opening and a second opening that are aligned in a first direction;
a first substrate vibrating film that closes off the first opening and the second opening;
a first piezoelectric element and a second piezoelectric element being disposed corresponding to the first opening and the second opening, respectively, on the first substrate vibrating film;
a second substrate having a third opening and a fourth opening that are aligned in the first direction;
a second substrate vibrating film that closes off the third opening and the fourth opening;
a third piezoelectric element and a fourth piezoelectric element being disposed corresponding to the third opening and the fourth opening, respectively, on the second substrate vibrating film; and
a support body having a first surface and a second surface that face away from each other in an opposite direction, the opposite direction intersecting with the first direction, the support body supporting the first substrate and the second substrate at a side of the first surface,
the first substrate and the second substrate being aligned in a second direction that intersects with the first direction and the opposite direction, and being spaced apart from each other in the second direction.

* * * * *